United States Patent

Sasaki et al.

(10) Patent No.: US 8,043,639 B2
(45) Date of Patent: Oct. 25, 2011

(54) PROCESS FOR PRODUCING WHEY PROTEIN-ENRICHED FERMENTED MILK OF AGITATED TYPE

(75) Inventors: Hitoshi Sasaki, Kanagawa (JP); Hiroyuki Nakagoshi, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 183 days.

(21) Appl. No.: 12/212,853

(22) Filed: Sep. 18, 2008

(65) Prior Publication Data

US 2009/0068312 A1 Mar. 12, 2009

Related U.S. Application Data

(63) Continuation of application No. PCT/JP2007/058689, filed on Apr. 16, 2007.

(30) Foreign Application Priority Data

Apr. 18, 2006 (JP) ................................ 2006-114200

(51) Int. Cl.
*A23C 21/00* (2006.01)
(52) U.S. Cl. ........... 426/41; 426/580; 426/583; 426/657
(58) Field of Classification Search .................... 426/34, 426/41, 580, 582, 583, 657
See application file for complete search history.

(56) References Cited

U.S. PATENT DOCUMENTS

| 5,156,956 A | 10/1992 | Motoki et al. |
| 5,681,598 A * | 10/1997 | Kuraishi et al. ................. 426/36 |
| 5,907,031 A | 5/1999 | Soeda et al. |
| 6,716,461 B2 | 4/2004 | Miwa et al. |
| 2001/0053398 A1 | 12/2001 | Soeda |
| 2007/0134374 A1 | 6/2007 | Boenisch et al. |

FOREIGN PATENT DOCUMENTS

| JP | 64-27471 | | 2/1989 |
| JP | 6-197688 | | 7/1994 |
| JP | 06197688 | * | 7/1994 |
| JP | 7-104 | | 1/1995 |
| JP | 2000-4786 | | 1/2000 |
| JP | 2000-262222 | | 9/2000 |
| WO | 01/70042 | | 9/2001 |

OTHER PUBLICATIONS http://en.wikipedia.org/wiki/Whey (2010).
Farnsworth et al., *Small Ruminant Research*, vol. 65, pp. 113-121 (2006).
Jaros et al., *Journal of Texture Studies*, vol. 37, pp. 113-155 (2006).

* cited by examiner

*Primary Examiner* — Leslie Wong
(74) *Attorney, Agent, or Firm* — Oblon, Spivak, McClelland, Maier & Neustadt, L.L.P.

(57) ABSTRACT

Mixing milk with a reaction product, which is prepared by dissolving at a high concentration highly pure milk whey protein having been separated from cow's milk, etc. and concentrated and then treating with transglutaminase, then inoculating with a lactic acid bacterium and fermenting economically affords a yogurt of agitated type, which is enriched in whey protein, shows little water release and has a rich feeling and a highly smooth texture.

20 Claims, No Drawings

PROCESS FOR PRODUCING WHEY PROTEIN-ENRICHED FERMENTED MILK OF AGITATED TYPE

CROSS REFERENCES TO RELATED APPLICATIONS

This application is a continuation of International Patent Application No. PCT/JP2007/058689, filed on Apr. 16, 2007, and claims priority to Japanese Patent Application No. 114200/2006, filed on Apr. 18, 2006, both of which are incorporated herein by reference in their entireties.

BACKGROUND OF THE INVENTION

1. Field of the Invention

The present invention relates to methods for producing stirred type fermented milk enriched with a whey protein. The present invention also relates to stirred type fermented milk enriched with a whey protein prepared by such a process.

2. Discussion of the Background

With respect to the quality of fermented milk such as yogurt, little water separation and high viscosity are regarded to be important as factors to determine the appearance and the texture of fermented milk. In order to improve these factors, a method of condensing raw material milk, a method of adding powdered skim milk, a method of adding a whey protein obtained by separation and condensation of whey produced from cow milk in a production of cheese, casein or the like, a method of adding a thickening polysaccharide or a method of adding a transglutaminase or the like is often used.

In particular, the addition of a milk whey protein and the use of a transglutaminase can prevent water separation and increase the viscosity without significantly changing the original flavor and texture of fermented milk.

Incidentally, fermented milk (yogurt) is roughly classified into a stirred type fermented milk (so-called early-fermentation yogurt) and a set type fermented milk (so-called late-fermentation yogurt) in accordance with its production method. In the case where a whey protein is used for a stirred type fermented milk, as shown in Japanese Patent Application Publication No. JP-A-7-104, the resulting yogurt has a coarse-grained structure, therefore, there has been a disadvantage that the resulting yogurt is likely to have a non-smooth texture.

Such a tendency becomes prominent as the addition amount of a whey protein is increased or the storage period of the resulting yogurt is longer. Therefore, even if it is intended to obtain a high effect by using a whey protein, it is difficult to increase the addition amount of a whey protein. Accordingly, there has been a limit on the improvement of the quality of stirred type fermented milk by using a milk whey protein.

In the case where a transglutaminase is used for fermented milk, as disclosed in Japanese Patent Application Publication No. JP-A-6-197688, a case in which a raw material milk is treated with a transglutaminase in advance prior to a fermentation step is common. In this case, it is necessary to retain the raw material milk and to subject the raw material milk to an enzymatic reaction, therefore, a large tank with a capacity equal to or greater than the production amount of the fermented milk is occupied during the enzymatic reaction time, and also an additional cost is required for an energy for maintaining a temperature necessary for the enzymatic reaction, and thus, there has been a disadvantage that the equipment use efficiency and energy efficiency are decreased. Further, a transglutaminase is still an expensive material, therefore, in comparison with other materials, a price advantage is not necessarily high.

In the production of a stirred type fermented milk, an attempt was also made in which a whey protein and a transglutaminase were added to a raw material milk and the resulting mixture was subjected to an enzymatic reaction thereby trying to obtain an synergistic improvement effect of both substances, however, the effect remained at an additive level, and an economical advantage was not observed.

Japanese Patent Application Publication No. JP-A-2000-4786 discloses a method comprising allowing a transglutaminase to act on a solution of a milk whey protein, and thereafter mixing the resulting reaction mixture in a raw material milk. According to this method, a yogurt, which has a smooth texture and goes down smoothly when swallowing, can be obtained. However, what is disclosed in the document is only a so-called late-fermentation yogurt obtained without crushing gel by stirring or the like, and the method does not apply to a stirred type yogurt, which is an object of the present invention.

SUMMARY OF THE INVENTION

Accordingly, it is one object of the present invention to provide novel methods for economically producing a stirred type yogurt, which is enriched with a milk whey protein, shows little water separation, gives a rich feel and has a smooth structure.

It is another object of the present invention to provide novel stirred type yogurts, which are enriched with a milk whey protein, show little water separation, give a rich feel and have a smooth structure.

These and other objects, which will become apparent during the following detailed description, have been achieved by the inventors' discovery that they could achieve the above object by a method comprising allowing a transglutaminase to act on a solution in which a milk whey protein of high purity obtained by separation from cow milk followed by condensation of the resulting substance is dissolved at a high concentration, and thereafter mixing the resulting reaction mixture in a raw material milk, and thus the present invention has been completed. That is, the present invention provides:

(1) A production method for a stirred type fermented milk, characterized by adding to a raw material milk a reaction product obtained by allowing a transglutaminase to react with a whey protein solution wherein the solid content in the aqueous solution is from 3 to 30% and the protein content in the solids is from 80 to 100% and thereafter fermenting the resulting mixture by inoculating a lactic acid bacterium.

(2) The production method according to (1), wherein the addition amount of the transglutaminase to the whey protein solution is from 0.5 to 5 units/g of protein and the temperature during the reaction is from 50° C. to 65° C.

According to the present invention, a stirred type yogurt, which shows little water separation, gives a rich feel and has a smooth structure can be economically produced.

DETAILED DESCRIPTION OF THE PREFERRED EMBODIMENTS

The milk whey protein solution to be used in the invention may be a whey protein solution in which the protein content in the solids is from 80% to 100%, preferably from 90 to 100%, and the solid content in the aqueous solution is from 3% to 30%, preferably from 7% to 20%. The raw material, the production method and the like of the milk whey protein are not particularly limited, and a substance obtained by condensing and separating whey produced when cheese or casein is produced from cow milk, a substance obtained by adding water to a substance obtained through drying and powdering of the above condensed and separated substance and dissolving the resulting powder in water or the like can be used.

When the protein content in the solids is 80% or less, the rate of the transglutaminase reaction decreases. Probably, the reason is considered that the amount of a substance that inhibits the transglutaminase activity is relatively increased when the protein content in the solids is lower.

In general, it is considered that as the concentrations of the substrate and the enzyme are higher, the rate of the enzymatic reaction increases, however, in the case where a milk whey protein is used as a substrate, when the condition does not fall within the above-mentioned range, the rate of the enzymatic reaction decreases. Further, in the case where the solid content is low, the volume of a tank to be used during the enzymatic reaction becomes large, therefore, an economical advantage is deteriorated.

The transglutaminase to be used in the invention is not particularly limited in terms of its origin as long as it has a transglutaminase activity, and for example, a transglutaminase derived from a microorganism belonging to the genus *Streptomyces* or the like (see, Japanese Patent Application Publication No. JP-A-64-27471), a transglutaminase derived from a mammal such as a guinea pig (see, Japanese Patent No. JP-B-1-50382), a transglutaminase derived from a fish such as codfish (see, Nobuo Seki et al., Abstracts for the Autumn Meeting of the Japanese Society of Fisheries Science, 1988, p. 167), a transglutaminase obtained by a genetic recombination technique utilizing biotechnology (see, Japanese Patent Application Publication No. JP-A-1-30889 and Japanese Patent Application Publication No. JP-A-6-225775) or the like can be used. In addition, a transglutaminase which is commercially available from Ajinomoto Co., Inc. under the trade name of "Activa" may be purchased and used.

As described above, as the transglutaminase, any can be used regardless of its origin and type as long as it is a transglutaminase. Further, either a transglutaminase of a type which requires calcium for the expression of its activity (a calcium-dependent transglutaminase) or a transglutaminase of a type which does not require calcium for the expression of its activity (a calcium-independent transglutaminase) can be used. However, it is preferred that a transglutaminase derived from a microorganism is used for the reasons that it can be used without calcium, it can be obtained in a large amount and the like.

The activity unit of the transglutaminase used in the invention is measured and defined as follows. That is, the transglutaminase is allowed to act in a reaction system containing benzyloxycarbonyl-L-glutamylglycine and hydroxylamine as substrates at a temperature of 37° C. in Tris buffer at pH 6.0, and resulting hydroxamic acid is formed into a ferric complex in the presence of trichloroacetic acid, and then an absorbance at 525 nm is measured. The amount of hydroxamic acid is calculated from a calibration curve, and an enzyme which produces 1 μmol of hydroxamic acid per minute is defined as 1 unit (1 U) (see, Japanese Patent Application Publication No. JP-A-64-27471).

In the invention, the modification of a whey protein by a transglutaminase can be performed by adding a transglutaminase to a whey protein solution and thereafter allowing the enzymatic reaction to proceed by, for example, letting the resulting mixture stand or stirring it.

The addition amount of a transglutaminase is preferably from 0.5 to 5 units per gram of the protein although it depends also on the reaction time and temperature. When the addition amount is less than 0.5 units per gram of the protein, it is difficult to obtain an effect or a required reaction time is prolonged. On the other hand, when the addition amount exceeds 5 units, an effect relative to the addition amount is significantly decreased, therefore, an economical advantage is lost.

The temperature during the enzymatic reaction is preferably from 50° C. to 65° C. When the temperature is lower than 50° C., the enzymatic reaction proceeds slowly, and also the growth of microorganisms cannot be suppressed, therefore, it is not preferred from a hygiene point of view. When the temperature exceeds 65° C., inactivation of a transglutaminase becomes prominent, therefore, an effect relative to the addition amount is significantly decreased.

The required reaction time depends also on the addition amount of a transglutaminase and the temperature during the reaction, however, in the case of 50° C. or higher, a sufficient effect can be obtained if the transglutaminase is allowed to react for about 10 minutes to about 5 hours. A solution of the thus obtained modified whey protein is added to a raw material milk of a yogurt in an amount of 0.05% to 3%, preferably 0.1% to 1% of the raw material milk in terms of the weight of the whey protein. Also from this, it is found that the used amount of a transglutaminase relative to a raw material milk is very small and the present invention is economically advantageous.

After a solution of the thus obtained modified whey protein is added to a raw material milk of a yogurt, the resulting mixture is sterilized by heating, and then a lactic acid bacterium is inoculated into the mixture, and fermented milk curds are obtained under a general condition. As the lactic acid bacterium, a lactic acid bacterium commonly used for a yogurt may be used. Further, as for the inoculation of a lactic acid bacterium, a lactic acid bacterium may be added or a commercially available yogurt containing a lactic acid bacterium may be added as such.

Subsequently, the curds are crushed by a procedure such as stirring or high-pressure emulsification to make the resulting product smooth, whereby a stirred type yogurt is obtained.

In this connection, the modified whey protein solution may be heated before it is mixed in a raw material milk of a yogurt so as to effect sterilization and inactivate a transglutaminase. Further, the modified whey protein solution is dried thereby obtaining modified whey protein powder and the powder may be directly mixed in a raw material milk or an aqueous solution of the powder may be mixed in a raw material milk of a yogurt.

Other features of the invention will become apparent in the course of the following descriptions of exemplary embodiments which are given for illustration of the invention and are not intended to be limiting thereof.

EXAMPLES

Example 1

To 10 parts of a whey protein isolate (Alacen 895 manufactured by Fontera Co, protein content: 94%), 90 parts of water was added and mixed, whereby a whey protein solution was obtained. Further, a transglutaminase preparation for a yogurt manufactured by Ajinomoto Co., Inc., "Activa" TG-YG (transglutaminase activity: 100 units/g, glutathione contained: 3.6%) was added thereto in accordance with Table 1, and the resulting mixture was left to stand at a temperature of 55° C. for 60 minutes, whereby a modified whey protein solution was obtained.

TABLE 1

| | Addition amount of TG-YG (parts) | Addition amount of transglutaminase (units/g of protein) |
|---|---|---|
| Comparative product 1 | 0 | 0 |
| Present inventive product 1 | 0.047 | 0.5 |
| Present inventive product 2 | 0.094 | 1 |
| Present inventive product 3 | 0.47 | 5 |
| Present inventive product 4 | 0.94 | 10 |

On the other hand, 53 parts of commercially available pasteurized cow milk, 4.8 parts of powdered skim milk and 39.5 parts of water were mixed, whereby a yogurt mix was obtained. To 94 parts of this yogurt mix, 3 parts of the above-mentioned modified whey protein solution (corresponding to the addition of a whey protein in an amount of 0.5% of the raw material milk) was added.

Then, the temperature of the mixture was immediately raised and maintained at 95° C. for 5 minutes. Thereafter, the mixture was cooled to 43° C., and 3 parts of a commercially available stirred type yogurt (containing a lactic acid bacterium) was added thereto and the temperature of the mixture was maintained at 43° C. thereby allowing the fermentation to proceed. When the pH of the mixture reached 4.6, the mixture was cooled to 20° C., and passed through a high-pressure homogenizer (LAB 1000, APV Co.) at a preset pressure of 0 bar, whereby a stirred type yogurt was obtained. This stirred type yogurt was packed in a container and stored under refrigeration for 7 days, and then, evaluation was performed. The evaluation results are shown in Table 2 and Table 3. As a control, a yogurt was prepared in the same procedure as above except that 3 parts of water was added in place of 3 parts of the whey protein solution.

TABLE 2

| | State of water separation | State of structure |
|---|---|---|
| Control | Significant water separation | Smooth structure |
| Comparative product 1 | Water separation | Coarse structure and rough surface |
| Present inventive product 1 | No water separation | Smooth structure and shiny surface |
| Present inventive product 2 | No water separation | Smooth structure and shiny surface |
| Present inventive product 3 | No water separation | Smooth structure and shiny surface |
| Present inventive product 4 | No water separation | Smooth structure and shiny surface |

TABLE 3

| | Texture |
|---|---|
| Control | Very runny and watery |
| Comparative product 1 | Comparative product 1 has a higher viscosity and is richer than the control, but is thinner and more watery than the present invention 1. |
| Present inventive product 1 | Present inventive product 1 has a higher viscosity and is richer than Comparative product 1, and is not watery. |
| Present inventive product 2 | Present inventive product 2 has a higher viscosity and is richer than Present inventive product 1, and is not watery. |
| Present inventive product 3 | Present inventive product 3 has a higher viscosity and is richer than Present inventive product 2, and is not watery. |

TABLE 3-continued

| | Texture |
|---|---|
| Present inventive product 4 | Comparative product 2 is equivalent to Present inventive product 3. |

As shown in the above, compared with the yogurt obtained by using a whey protein which was not modified by a transglutaminase, the yogurt obtained by using a whey protein which was modified by a transglutaminase showed no water separation, and gave a preferred rich feel without deteriorating a smooth texture.

INDUSTRIAL APPLICABILITY

According to the present invention, a stirred type yogurt, which shows little water separation, gives a rich feel and has a smooth structure can be economically produced, therefore, the invention is extremely useful in the field of food industry.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A process of making a stirred type fermented milk, said process comprising:
   (i) adding, to a raw material milk, a reaction product which is obtained by reacting a transglutaminase with a whey protein solution, to obtain a mixture; and
   (ii) fermenting said mixture by inoculating a lactic acid bacterium, wherein said whey protein solution has a solid content of from 3 to 30 wt. %, based on the total weight of said whey protein solution, and a protein content of from 80 to 100 wt. %, based on the weight of solids in said whey protein solution.

2. The process according to claim 1, wherein said transglutaminase is added to said whey protein solution in an amount of from 0.5 to 5 units of transglutaminase per gram of protein in said whey protein solution and said reacting is carried out at a temperature of from 50° C. to 65° C.

3. The process according to claim 1, wherein said whey protein solution has a solid content of from 7 to 20 wt. %, based on the total weight of said whey protein solution, and a protein content of from 90 to 100 wt. %, based on the weight of solids in said whey protein solution.

4. The process according to claim 1, wherein said transglutaminase is reacted with said whey protein solution for a time of from 10 minutes to 5 hours.

5. The process according to claim 1, wherein said reaction product is added to said raw material milk in an amount such that the amount of whey protein added to said raw material milk is 0.05 to 3 wt. %, based on the total weight of said raw material milk.

6. The process according to claim 1, wherein said reaction product is added to said raw material milk in an amount such that the amount of whey protein added to said raw material milk is 0.1 to 1 wt. %, based on the total weight of said raw material milk.

7. The process according to claim 1, wherein said reaction product is heated to deactivate the transglutaminase prior to said adding to said raw material milk.

8. The process according to claim 1, wherein said reaction product is dried to obtain a powder and said powder is added to said raw material milk.

9. The process according to claim 1, wherein said reaction product is dried to obtain a powder, said powder is mixed with water to form an aqueous mixture, and said aqueous mixture is added to said raw material milk.

10. A process of making a stirred type fermented milk, said process comprising:
  (i) reacting a transglutaminase with a whey protein solution, to obtain a reaction product;
  (ii) adding said reaction product to a raw material milk, to obtain a mixture;
  (iii) inoculating said mixture with a lactic acid bacterium, to obtain an inoculated mixture; and
  (iv) fermenting said inoculated mixture, to obtain a fermented milk,
  wherein said whey protein solution has a solid content of from 3 to 30 wt. %, based on the total weight of said whey protein solution, and a protein content of from 80 to 100%, based on the weight of solids in said whey protein solution.

11. The process according to claim 10, wherein said transglutaminase is reacted with said whey protein solution in an amount of from 0.5 to 5 units of transglutaminase per gram of protein in said whey protein solution and said reacting is carried out at a temperature of from 50° C. to 65° C.

12. The process according to claim 10, wherein said whey protein solution has a solid content of from 7 to 20 wt. %, based on the total weight of said whey protein solution, and a protein content of from 90 to 100 wt. %, based on the weight of solids in said whey protein solution.

13. The process according to claim 10, wherein said transglutaminase is reacted with said whey protein solution for a time of from 10 minutes to 5 hours.

14. The process according to claim 10, wherein said reaction product is added to said raw material milk in an amount such that the amount of whey protein added to said raw material milk is 0.05 to 3 wt. % based on the total weight of said raw material milk.

15. The process according to claim 10, wherein said reaction product is added to said raw material milk in an amount such that the amount of whey protein added to said raw material milk is 0.1 to 1 wt. % based on the total weight of said raw material milk.

16. The process according to claim 10, wherein said reaction product is heated to deactivate the transglutaminase prior to said adding to said raw material milk.

17. The process according to claim 10, wherein said reaction product is dried to obtain a powder and said powder is added to said raw material milk.

18. The process according to claim 10, wherein said reaction product is dried to obtain a powder, said powder is mixed with water to form an aqueous mixture, and said aqueous mixture is added to said raw material milk.

19. A stirred type fermented milk, which is prepared by a process according to claim 1.

20. A stirred type fermented milk, which is prepared by a process according to claim 10.

* * * * *